(12) United States Patent
Vind

(10) Patent No.: US 6,783,941 B2
(45) Date of Patent: Aug. 31, 2004

(54) METHOD FOR PRODUCING A POLYNUCLEOTIDE LIBRARY IN VITRO BY MISMATCH REPAIR OF HETERODUPLEXES

(75) Inventor: Jesper Vind, Vaerlose (DK)

(73) Assignee: Novozymes A/S, Bagsvaerd (DK)

( * ) Notice: Subject to any disclaimer, the term of this patent is extended or adjusted under 35 U.S.C. 154(b) by 204 days.

(21) Appl. No.: 10/004,993

(22) Filed: Dec. 5, 2001

(65) Prior Publication Data

US 2003/0017477 A1 Jan. 23, 2003

Related U.S. Application Data

(60) Provisional application No. 60/256,018, filed on Dec. 15, 2000.

(30) Foreign Application Priority Data

| Dec. 6, 2000 | (DK) | 2000 01828 |
| Dec. 11, 2000 | (DK) | 2000 01853 |

(51) Int. Cl.$^7$ .......................... C12Q 1/68; C12P 19/34
(52) U.S. Cl. ........................ 435/6; 435/91.1; 435/91.2; 536/25.3
(58) Field of Search .................. 435/6, 91.1, 91.2; 536/25.3

(56) References Cited

U.S. PATENT DOCUMENTS

| 5,334,522 A | 8/1994 | Resnick et al. ........... 435/172.3 |
| 6,537,746 B2 * | 3/2003 | Arnold et al. .................. 435/6 |

FOREIGN PATENT DOCUMENTS

| WO | 93/20233 | 10/1993 |
| WO | 97/21837 | 6/1997 |
| WO | 98/13483 | 4/1998 |
| WO | 98/41653 | 9/1998 |
| WO | 99/29902 | 6/1999 |
| WO | 00/00632 | 1/2000 |
| WO | 00/50567 | 8/2000 |
| WO | 01/348353 A2 | 5/2001 |
| WO | 02/24953 A1 | 3/2002 |
| WO | 02/46396 * | 6/2002 | ........... C12N/15/10 |

OTHER PUBLICATIONS

Sugahara et al., The EMBO Journal, vol. 19, No. 15, pp. 3857–3869 (2000).
Biswas et al., The Journal Of Biological Chemistry, vol. 271, No. 9, pp. 5040–5048 (Mar. 1, 1996).
Volkov et al., "Random Chimeragenesis by Heteroduplex Recombination" vol. 27, p. 456–463, (2000).
Volkov et al, "Recombination and Chimeragenesis by in vitro heteroduplex formation and in vivo repair", 1999 Oxford University Press Nucleic Acids Research, 1999 vol. 27, No. 18.
Cami et al, "Correction of complex heteroduplexes made of mouse H–2 gene sequences in *Escherichia coli* K–12", Proc. Natl. Acad. Sci. USA vol. 81, pp. 503–507, Jan. 1984 genetics.
Chang et al, "Recombination following transformation of *Escherichia coli* by heteroduplex plasmid DNA molecules", Gene, 29 (1984) 255–261 Elsevier.
Abastado et al, "Processing of complex heteroduplexes in *Escherichia coli* and Cos–1 monkey cells", Proc. Natl. Acad. Sci. USA vol. 81, pp. 5792–5796, Sep. 1984 Genetics.

* cited by examiner

*Primary Examiner*—Kenneth R. Horlick
(74) *Attorney, Agent, or Firm*—Elias Lambiris; Jason Garbell

(57) ABSTRACT

A method for making polynucleotide libraries that comprise new recombined polynucleotides by using mismatch repair enzymes or proteins to shuffle at least two variants of the same polynucleotide or at least two homologous polynucleotides through a Recombinatorial Chain Reaction, RCR.

17 Claims, No Drawings

METHOD FOR PRODUCING A POLYNUCLEOTIDE LIBRARY IN VITRO BY MISMATCH REPAIR OF HETERODUPLEXES

CROSS-REFERENCE TO RELATED APPLICATIONS

This application claims, under 35 U.S.C. 119, the benefit of Danish application no. PA 2000 01828, filed Dec. 6, 2000, and PA 2000 01853 filed on Dec. 11, 2000 and U.S. provisional application No. 60/256,018, filed Dec. 15, 2000, the contents of which are fully incorporated herein by reference.

FIELD OF INVENTION

A method for making a plurality of new recombined polynucleotides by using a mismatch repair protein(s) or enzyme(s) to recombine at least two variants of the same polynucleotide or at least two homologous polynucleotides by Recombinatorial Chain Reaction, RCR.

BACKGROUND OF THE INVENTION

The mismatch repair system is a system within cells which recognizes strand-strand nucleotide mismatches in newly synthesized duplex DNA sequences by comparing the new polynucleotide strand with the "old" polynucleotide strand originating from the parental duplex DNA, especially following DNA replication. The mismatch repair system of e.g. *Escherichia coli* corrects the strand-strand nucleotide mismatches by using the methylated "old" strain of the new duplex DNA as a template.

Independently of the molecular mechanism, the mismatch repair system normally limits the genetic diversity within a cell; where diversity in this context means the number of different DNA sequences. For example, a heteroduplex polynucleotide which comprises a single mismatch represents a diversity of two, since after one round of replication, the heteroduplex with the mismatch will have become two different double-stranded homoduplexes (with a one base pair difference between the two, originating from the mismatch in the parental heteroduplex).

However if the mismatch repair system corrects the mismatch in a heteroduplex before replication, the result will be two identical homoduplex DNA sequences, consequently the genetic diversity would be reduced to only one.

Several strategies and methods for generating genetic diversity are known in the art, such as classical random mutagenesis, site-directed mutagenesis, gene-shuffling etc. However, there is still a need for new methods and ways to produce diverse polynucleotide sequences that may encode polypeptides with new properties or may have new properties themselves.

The state of the art shuffling methods are very efficient in shuffling polynucleotides comprising mutations that are located far apart in the polynucleotide sequences. However, shuffling or recombining mutations that are positioned in relative close vicinity within a polynucleotide molecule has remained a challenge so far.

The present invention provides a method of utilizing a mismatch repair protein(s) or enzyme(s) to increase the genetic diversity in a polynucleotide population from a starting material of at least two homologous polynucleotides, to obtain a plurality of new recombined homologous polynucleotides. The method of the invention even allows for the shuffling or recombining of homologous polynucleotide sequences, where the sequence variation(s) between the at least two parental starting sequences are closely located in the polynucleotide sequence.

The method of the invention utilizes a mismatch repair protein(s) as known in the art (Biswas and Hsieh, 1996, Identification and Characterization of a Thermostable MutS Homologue from *Thermus aquaticus*, J Biol Chem 271(9):5040–5048) and (Sugahara et al., 2000, Crystal structure of a repair enzyme of oxidatively damaged DNA, MutM (Fpg), from an extreme thermophile, *Thermus thermophilus* HB8, J EMBO 19(15):3857–3869).

SUMMARY OF THE INVENTION

The problem to be solved by the present invention is how to generate diverse polynucleotide libraries that comprise new recombined polynucleotides, from a starting material comprising homologous template polynucleotides. A cell population comprising such a library may then be used to screen for a particular property/activity of interest encoded by a polynucleotide which can be selected on this basis. Also polynucleotide sequences with particular changed or improved properties might be selected, such as promoters, terminators and other regulatory elements.

The present inventor provides a method for increasing the genetic diversity from a starting material of at least two homologous double-stranded polynucleotides or at least two variants of the same double-stranded polynucleotides such as two different DNA sequences encoding homologous polypeptides e.g. enzymes or pharmaceutically active peptides.

As mentioned above, the present invention even allows shuffling or recombining of homologous polynucleotide sequences, where the sequence variation(s) between the at least two parental starting sequences are closely located in the polynucleotide sequence e.g. the two starting sequences may comprise variations that are only one or a few nucleotides away from each other.

Optionally the steps (b) through (d) of the method of the present invention may be repeated for one or more cycles; wherein the new duplexes of step (d) serve as new template polynucleotides in step (b) in each subsequent cycle. Increasing the number of repeats or cycles will result in an increase in the number of new recombined polynucleotides, as new permutations of mismatches will be generated in the annealing step of each cycle.

Accordingly, in a first aspect the present invention relates to a method for forming a plurality of recombined homologous double-stranded polynucleotides from at least two homologous double-stranded template polynucleotides, said method comprising the steps of:

a) providing a solution comprising at least two non-methylated homologous double-stranded template polynucleotides and one or more mismatch repair protein(s);

b) denaturing the template polynucleotides into single-stranded polynucleotides;

c) annealing the different single-stranded polynucleotides, wherein heteroduplexes are formed;

d) allowing the mismatch repair protein(s) to repair nucleotide mismatches in the heteroduplexes, wherein recombined new duplexes are formed; and e) optionally, repeating steps b) through d) for one or more cycles; wherein the new duplexes of step d) serve as new template polynucleotides in step b) in each subsequent cycle.

In a second aspect the present invention relates to a plurality of recombined nucleotides generated by a method as defined in the first aspect.

A library of recombined polynucleotides generated by the method of the invention may be screened for a particular activity or property of interest, and a polynucleotide may be selected based on the results of such a screening.

Accordingly, in a third aspect the invention relates to a recombined polynucleotide generated by a method as defined in the first aspect.

Also, in a fourth aspect the invention relates to the use of a plurality of recombined polynucleotides of the second aspect generated by a method as defined in the first aspect, in a screening assay for an activity or property of interest.

In a final aspect the invention relates to the use of a recombined polynucleotide of the third aspect generated by a method as defined in the first aspect, for expression or production of a polypeptide of interest.

DEFINITIONS

Following section provides definitions of technical features in above mentioned aspects of the invention.

The term "a gene" denotes herein a gene (a polynucleotide) which is capable of being expressed into a polypeptide within a living cell or by an appropriate expression system. Accordingly, said gene is defined as an open reading frame starting from a start codon (normally "ATG", "GTG", or "TTG") and ending at a stop codon (normally "TAA", TAG" or "TGA"). In order to express said gene there must be elements, as known in the art, in connection with the gene, necessary for expression of the gene within the cell. Such standard elements may include a promoter, a ribosomal binding site, a termination sequence, and maybe others elements as known in the art.

The term "substantially pure polynucleotide" as used herein refers to a polynucleotide preparation, wherein the polynucleotide has been removed from its natural genetic milieu, and is thus free of other extraneous or unwanted coding sequences and is in a form suitable for use within genetically engineered protein production systems.

Thus, a substantially pure polynucleotide contains at the most 10% by weight of other polynucleotide material with which it is natively associated (lower percentages of other polynucleotide material are preferred, e.g. at the most 8% by weight, at the most 6% by weight, at the most 5% by weight, at the most 4% at the most 3% by weight, at the most 2% by weight, at the most 1% by weight, and at the most ½% by weight). A substantially pure polynucleotide may, however, include naturally occurring 5' and 3' untranslated regions, such as promoters and terminators.

It is preferred that the substantially pure polynucleotide is at least 92% pure, i.e. that the polynucleotide constitutes at least 92% by weight of the total polynucleotide material present in the preparation, and higher percentages are preferred such as at least 94% pure, at least 95% pure, at least 96% pure, at least 96% pure, at least 97% pure, at least 98% pure, at least 99%, and at the most 99.5% pure.

The polynucleotides disclosed herein are preferably in a substantially pure form. In particular, it is preferred that the polynucleotides disclosed herein are in "essentially pure form", i.e. that the polynucleotide preparation is essentially free of other polynucleotide material with which it is natively associated. Herein, the term "substantially pure polynucleotide" is synonymous with the terms "isolated polynucleotide" and "polynucleotide in isolated form".

The term "homologous" in the present context means that the two homologous polynucleotides or polypeptides have a "degree of identity" of at least 60%, more preferably at least 70%, even more preferably at least 85%, still more preferably at least 90%, more preferably at least 95%, and most preferably at least 98%. Whether two polynucleotide or polypeptide sequences have a sufficiently high degree of identity to be homologous as defined herein, can suitably be investigated by aligning the two sequences using a computer program known in the art, such as "GAP" provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–453). Using GAP with the following settings for DNA sequence comparison: GAP creation penalty of 5.0 and GAP extension penalty of 0.3.

A "heteroduplex" is used herein as having the meaning known in the art, which means that a heteroduplex is a double-stranded polynucleotide, such as a double-stranded DNA-molecule, wherein several base- or nucleotide-pairs are mismatched or, in other words, the two strands are not perfectly complementary.

The term "homoduplex" has the well-described meaning known in the art, a double-stranded polynucleotide wherein the two strands are perfectly complementary and no nucleotide-pair mismatches are found i.e. all adenosines pair with a thymidine (A's pair with T's) and all guanosines pair with a cytidine (G's pair with C's).

The term "duplex" as used herein is defined as a double-stranded polynucleotide which may be either a hetero- or a homoduplex polynucleotide as defined above.

The term "denaturing" is used herein as known in the art, for example a double-stranded polynucleotide comprised in a liquid solution may be denatured by heating the solution to at least the melting-point or melting-temperature of the double-stranded polynucleotide and keeping the solution at that temperature until the double-stranded polynucleotide has denatured, separated, or "melted" into two complementary single-stranded polynucleotides.

"Annealing" as used herein means that conditions such as temperature and salt-concentrations in a liquid solution are so that a single-stranded polynucleotide comprised in the solution will anneal preferentially to another single-stranded homologous polynucleotide comprised in the solution, in other words polynucleotides that are not homologous will not anneal to any significant extent.

"Nucleic acid construct" when used herein, the term nucleic acid construct means a nucleic acid molecule, either single- or double-stranded, which is isolated from a naturally occurring source or which has been modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

"Control sequence" is defined herein to comprise all components that are necessary or advantageous for the expression of a polynucleotide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

"Operably linked" is defined herein as a configuration in which a control sequence is appropriately placed at a position relative to the coding sequence of the polynucleotide sequence such that the control sequence directs the expression of the polynucleotide.

"Coding sequence" is intended to cover a polynucleotide sequence, which directly specifies the amino acid sequence of its protein product. The boundaries of the coding sequence are generally determined by an open reading frame, which usually begins with the ATG start codon. The coding sequence typically include DNA, cDNA, and recombinant nucleotide sequences.

In the present context, the term "expression" includes any step involved in the production of a polypeptide including, but not limited to, transcription, post-transcriptional modification, translation, post-translational modification, and secretion.

In the present context, the term "expression vector" covers a polynucleotide molecule, linear or circular, that comprises a polynucleotide segment encoding a polypeptide of interest, and which is operably linked to additional segments that provide for the expression.

The term "host cell", as used herein, is defined below.

The term "mismatch repair system" shall herein be understood according to the art, as a system normally present within cells which recognises mismatches in duplex DNA sequences; see e.g. WO 97/37011, page 1, line 21–28. The mismatch repair system either corrects the mismatches by e.g. using the methylated "old" strain as template or alternatively the system may mediate degradation of the duplex DNA sequences which comprise the mismatches. Independently of the precise molecular mechanism, the end result will be that the "mismatch repair system" normally limits the "diversity" within the cell, represented by those duplex DNA sequences that comprise mismatches. The instant invention however utilizes the very base pair mismatch-correcting property of the mismatch repair system to generate diversity instead of limiting it. When non-methylated double-stranded polynucleotides comprising mismatches are treated with a mismatch repair protein(s), the result will be unpredictable error-corrections in both strands, as there is no discernable template strand for the protein(s) to use for proofreading. This means that various new nucleotides may be introduced in either polynucleotide strand of the heteroduplex in the process of forming a new recombined duplex with a reduced number of mismatches or no mismatches at all. The mismatch repair system preferably comprises a MutS homologue, preferably MutS YT1 of *Thermus aquaticus*, or comprises a MutL homologue, a MSH2 homologue, a MSH6 homologue, a MutM homologue, a MutY homologue, a MutT homologue, a MutH homologue, a HexA homologue, a HexB homologue, or a GTBP/p160 homologue (Biswas and Hsieh, 1996, vide supra).

The term "solution" denotes any liquid solution, such as an aqueous solution, comprising the at least two homologous double-stranded template polynucleotides and one or more mismatch repair protein(s).

The term "DNA library", "polynucleotide library", or "plurality of polynucleotides" denotes herein a library of at least two different DNA sequences. For many practical purposes the library is much bigger. Accordingly, the DNA library preferably comprises at least 1000 different DNA sequences, more preferably at least 10000 different DNA sequences, and even more preferably at least 100000 different DNA sequences.

In the present context, the term "allelic variant" denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "thermostable" protein(s) in the present context means that the protein(s) remains essentially functional after having been exposed to the relatively high temperatures needed to denature the double-stranded polynucleotides in step (b) of the method of the invention. Specifically the thermostable protein(s) retains from at least 60% to 80% of its activity at its optimum temperature after one denaturing step; wherein the activity may be determined by the ATP-hydrolysis (ATPase) assay described in (Biswas and Hsieh, 1996, vide supra) which is incorporated herein by reference.

DETAILED DESCRIPTION OF THE INVENTION

A method for forming a plurality of recombined homologous double-stranded polynucleotides from at least two homologous double-stranded template polynucleotides according to the first aspect of the invention.

The techniques used to isolate or clone a polynucleotide sequence are known in the art and include isolation from genomic DNA, preparation from cDNA, or a combination thereof. The cloning of the polynucleotide sequences of the present invention from such genomic DNA can be effected, e.g., by using the well known polymerase chain reaction (PCR), expression cloning, or antibody screening of expression libraries to detect cloned DNA fragments with shared structural features. See, e.g., Innis et al., 1990, *PCR: A Guide to Methods and Application*, Academic Press, New York. Other amplification procedures such as ligase chain reaction (LCR), ligated activated transcription (LAT) and nucleotide sequence-based amplification (NASBA) may be used. The nucleotide sequence may be cloned from a bacterial or fungal strain or another or related organism and thus, for example, may be an allelic or is species variant of the polypeptide encoding region of the nucleotide sequence.

The polynucleotide sequence may be obtained by standard cloning procedures used in genetic engineering to relocate the polynucleotide sequence from its natural location to a different site where it will be reproduced. The cloning procedures may involve excision and isolation of a desired polynucleotide fragment comprising the polynucleotide sequence of interest, insertion of the fragment into a vector molecule, and incorporation of the resulting recombinant vector into a host cell where multiple copies or clones of the polynucleotide sequence will be replicated. The polynucleotide sequence may be of genomic, cDNA, RNA, semi synthetic, synthetic origin, or any combinations thereof.

Accordingly a preferred embodiment of the invention relates to a method of the first aspect, wherein the at least two homologous double-stranded template polynucleotides are obtained by PCR amplification.

There is a substantial commercial interest in polypeptides such as pharmaceutically active peptides or industrial enzymes, and there is much research focused on changing or improving the properties or activities of such polypeptides.

Terms like "protein engineering" or "gene shuffling" are frequently encountered in the art. The present invention provides a new way of recombining polynucleotide sequences without having to fragment the template polynucleotides or synthesize a large number of overlapping primers to be used in a PCR reaction etc.

The method of the invention allows specific non-determined sequence variations to be recombined between homologous annealed polynucleotides via the action of a mismatch repair protein(s) which exchanges nucleotides in the polynucleotide sequences where there is a mismatch between the homologous strands, to provide new recombined polynucleotide strands, thus increasing the genetic diversity. A requirement for the method to function is that at least two homologous polynucleotide strands are able to anneal under the conditions given and this ability will largely depend on the degree of identity between the two polynucleotide strands which should preferably be at least 60%, more preferably at least 70%, even more preferably at least 85%, still more preferably at least 90%, more preferably at least 95%, and most preferably at least 98%.

It is well known in the art that polynucleotide sequences encoding certain polypeptides with similar properties or activities, such as enzymes, are often highly homologous. The homologous polynucleotides and polypeptides may be species variants or allelic variants descending from a common ancestral sequence which have evolved separately to the present day.

A template polynucleotide may encode an enzymatic polypeptide e.g. an aminopeptidase, an amylase, a carbohydrase, a carboxypeptidase, a catalase, a cellulase, a chitinase, a cutinase, a cyclodextrin glycosyltransferase, a deoxyribonuclease, an esterase, an alpha-galactosidase, a beta-galactosidase, a glucoamylase, an alpha-glucosidase, a beta-glucosidase, a haloperoxidase, an invertase, a laccase, a lipase, a mannosidase, an oxidase, a pectinolytic enzyme, a peroxidase, a phytase, a polyphenoloxidase, a proteolytic enzyme, a ribonuclease, or a xylanase.

Consequently, a preferred embodiment of the invention relates to the method of the first aspect, wherein the at least two homologous double-stranded template polynucleotides encode homologous polypeptides, preferably having a degree of identity of at least 60%, more preferably at least 70%, even more preferably at least 85%, still more preferably at least 90%, more preferably at least 95%, and most preferably at least 98%.

Another preferred embodiment of the invention relates to a method of the first aspect, wherein the at least two homologous double-stranded template polynucleotides encode homologous enzymes, preferably amylases, proteases, cellulases, lipases, xylanases, or phospholipases.

The homologous template polynucleotides may be comprised in a population of host cells which do not methylate polynucleotides or the gene encoding the mismatch repair protein(s) may be comprised in the same population of cells or in another cell population so that the cells produce the repair protein(s). The cells may secrete the repair protein(s) or the cells may produce the repair protein(s) intracellularly; in the latter case it may be an advantage to lyse the cells prior to step (b) of the method of the invention.

Accordingly a preferred embodiment relates to a method of the first aspect, wherein the solution comprises a population of cells or a lysate of a population of cells.

Further, a preferred embodiment relates to a method of the first aspect, wherein the population of cells or the lysate of a population of cells comprises the at least two homologous double-stranded template polynucleotides.

Still another preferred embodiment relates to a method of the first aspect, wherein the population of cells or the lysate of a population of cells comprises the mismatch repair protein(s).

Yet another preferred embodiment relates to a method of the first aspect, wherein the population of cells, or the population of cells giving rise to the lysate, do not methylate newly synthesized polynucleotides.

As mentioned previously, the denaturing and annealing steps in the method of the invention can be achieved by raising and subsequently lowering the temperature of the solution, however that would require the mismatch repair protein(s) to remain essentially functional after having been exposed to the relatively high temperatures needed to denature the double-stranded polynucleotides. It may be advantageous to use a thermostable mismatch repair protein(s).

Accordingly a preferred embodiment relates to a method of the first aspect, wherein the mismatch repair protein(s) is (are) thermostable, preferably the thermostable mismatch repair protein(s) comprises a MutS homologue, preferably MutS YT1 of *Thermus aquaticus*, and more preferably the thermostable mismatch repair protein(s) comprises a MutL homologue, a MSH2 homologue, a MSH6 homologue, a MutM homologue, a MutY homologue, a MutT homologue, a MutH homologue, a HexA homologue, a HexB homologue, or a GTBP/p160 homolog.

As mentioned previously the denaturing step in the method of the invention may be achieved by increasing the temperature of the solution.

Accordingly a preferred embodiment relates to a method of the first aspect, wherein the denaturing is achieved by increasing the temperature of the solution, preferably to at least 90° C., more preferably to at least 91° C., more preferably to at least 92° C., even more preferably to at least 93° C., still more preferably to at least 94° C., more preferably to at least 95° C., and most preferably to at least 96° C.

As also mentioned above, the annealing step in the method of the invention may be performed by lowering the temperature of the solution, preferably by lowering the temperature at least to a temperature where the complementary homologous single-stranded polynucleotides preferentially anneal to each other and where the mismatch repair protein(s) functions.

Accordingly a preferred embodiment relates to a method of the first aspect, wherein the annealing is achieved by lowering the temperature of the solution, preferably at least to a temperature at which the micmatch repair protein(s) functions, more preferably at least to between 45° C. and 85° C., more preferably at least to between 50° C. and 80° C., more preferably at least to between 55° C. and 75° C., and most preferably at least to between 60° C. and 70° C.

We previously mentioned that the steps (b) through (d) of the method of the present invention may optionally be repeated for one or more cycles; wherein the new duplexes of step (d) serve as new template polynucleotides in step (b) in each subsequent cycle. Increasing the number of repeats or cycles will result in an increase in the number of new recombined polynucleotides, as new permutations of mismatches will be generated in the annealing step of each cycle.

Consequently a preferred embodiment relates to a method of the first aspect, wherein steps b) through d) are repeated for between 1 and 10 cycles; wherein the new duplexes of step d) serve as new template polynucleotides in step b) in each subsequent cycle.

Another preferred embodiment relates to a method of the first aspect, wherein steps b) through d) are repeated for at least 10 cycles; wherein the new duplexes of step d) serve as new template polynucleotides in step b) in each subsequent cycle.

A polynucleotide library obtained by the method of the invention may be expressed and assayed in a screen for a particular property/activity of interest encoded by a polynucleotide which can be selected on this basis. Also polynucleotide sequences with particular changed or improved properties might be selected, such as promoters, terminators and other regulatory elements.

The present invention also relates to nucleic acid constructs comprising a nucleotide sequence of the present invention operably linked to one or more control sequences that direct the expression of the coding sequence in a suitable host cell under conditions compatible with the control sequences.

A polynucleotide sequence of the present invention may be manipulated in a variety of ways to provide e.g. for expression of an encoded polypeptide. Manipulation of the nucleotide sequence prior to its insertion into a vector may be desirable or necessary depending on the expression vector. The techniques for modifying nucleotide sequences utilizing recombinant DNA methods are well known in the art.

The control sequence may be an appropriate promoter sequence, a nucleotide sequence which is recognized by a host cell for expression of the nucleotide sequence. The promoter sequence contains transcriptional control sequences, which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Accordingly a preferred embodiment relates to a method of the first aspect, wherein additional steps are performed, said additional steps comprising:

f) generating a gene library by cloning the plurality of recombined polynucleotides;

g) expressing and screening the gene library for an activity or property of interest; and h) isolating or identifying the recombined polynucleotide which gives rise to the activity or property of interest.

The present invention also relates to recombinant expression vectors comprising the polynucleotides of the invention especially when those are comprised in a nucleic acid construct such as an expression vector. The various nucleotide and control sequences described above may be joined together to produce a recombinant expression vector which may include one or more convenient restriction sites to allow for insertion or substitution of the polynucleotide sequence at such sites.

Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof.

Preferred for use in an Aspergillus cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination.

Alternatively, the vector may contain additional nucleotide sequences for directing integration by homologous recombination into the genome of the host cell. The additional nucleotide sequences enable the vector to be integrated into the host cell genome at a precise location(s) in the chromosome(s).

To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in Bacillus. Examples of origins of replication for use in a yeast host cell are the 2 micron origin of replication, ARS1, ARS4, the combination of ARS1 and CEN3, and the combination of ARS4 and CEN6. An example of a filamentous fungal stabilizing element is the AMA1 sequence. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

The present invention also relates to recombinant a host cell comprising the polynucleotide(s) or nucleic acid construct(s) of the invention, which are advantageously used in the screening assays described herein. A vector comprising a nucleotide sequence of the present invention is introduced into a host cell so that the vector is maintained as a chromosomal integrant or as a self-replicating extra-chromosomal vector as described earlier.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a Streptomyces cell, e.g., *Streptomyces lividans* or *Streptomyces murinus*, or gram negative bacteria such as *E. coli* and Pseudomonas sp.

In a preferred embodiment, the bacterial host cell is a *Bacillus lentus, Bacillus licheniformis, Bacillus stearothermophilus*, or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In an even more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

A plurality of recombined polynucleotides of the second aspect generated by the method of first aspect may be screened for a particular activity or property of interest, and a recombined polynucleotide of the third aspect generated by the method of the first aspect may be selected from the plurality of the second aspect based on the results of such a screening.

An essential element in this screening process it the use of a plurality of recombined nucleotides of the second aspect generated by a method of the first aspect, in a screening assay for an activity or property of interest.

EXAMPLES

Example 1

Construction of an Expression Plasmid

Plasmids pENI1298 and pENI1299 were described in WO 00/24883. The plasmid pENI1298 was further developed in order to decrease plasmid size (thus improve transformation), improve expression (by improving promoter), have expression in *E. coli* for improved library screening (by improving same promoter), ease cloning (by introducing unique restriction sites downstream of promoter), ease cloning (by using the Gateway cloning technology).

Plasmid pENI1960 was made using the Gateway Vector™ conversion system (Lifetechnology® cat no. 11828–019) by cutting pENI1902 with BamHI, filling the DNA ends using Klenow fragment polymerase and nucleotides (thus making blunt ends) followed by ligation to reading frame A Gateway™ PCR fragment. The cloning in the correct orientation was confirmed by sequencing.

Plasmid pENI1902 was made in order to have a promoter that works in both *E. coli* and Aspergillus. This was done by unique site elimination using the "Chameleon double stranded site-directed mutagenesis kit" as recommended by Stratagene®. Plasmid pENI1861 was used as template and the following primers were used as selection primers ("5'P" indicates a 5' phosphorylation of the primer):

177996 (SEQ ID NO:1): 5'P gaatgacttggttgacgcgtcaccagtcac 135640 (SEQ ID NO:2): 5'P cttattagtaggttggtacttcgag 135638 (SEQ ID NO:3): 5'P gtccccagagtagtgtcactatgtcgaggcagttaag The 080399J19 primer (SEQ ID NO:4) was used as mutagenic primer to introduce a −35 and −10 promoter consensus sequence (from *E. coli*) in the Aspergillus expression promoter. Introduction of the mutations was verified by sequencing.

080399J19 (SEQ ID NO:4):
5'P gtatgtcccttgacaatgcgatgtatca-catgatataattactagcaagggaagccgtgcttgg Plasmid pENI1861 was made in order to have the state of the art Aspergillus promoter in the expression plasmid, as well as a number of unique restriction sites for cloning. A PCR fragment (app. 620 bp) was made using pMT2188 (see Example 5) as template and the following primers:

051199J1 (SEQ ID NO:5):
5' cctctagatctcgagctcggtcaccggtggcctccgcggccgctggatccccagttgtg -continued 1298TAKA (SEQ ID NO:6):
5' gcaagcgcgcgcaatacatggtgttttgatcat The fragment was cut BssHII and Bgl II, and cloned into pENI1849 which was also cut with BssHII and Bgl II. The cloning was verified by sequencing.

Plasmid pENI1849 was made in order to truncate the pyrG gene to the essential sequences for pyrG expression, in order to decrease the size of the plasmid, thus improving transformation frequency. A PCR fragment (app. 1800 bp) was made using pENI1299 as template and the following primers:

270999J8
(SEQ ID NO:7): 5' tctgtgaggcctatggatctcagaac

270999J9
(SEQ ID NO:8): 5' gatgctgcatgcacaactgcacctcag

The PCR-fragment was cut with the restriction enzymes StuI and SphI, and cloned into pENI1298, also cut with StuI and SphI; the cloning was verified by sequencing.

Example 2

Preparation of a cell extract comprising MutS mismatch repair enzymes from *Thermus aquaticus* ATCC25105.

The cell extract is made as described by O'Grady G. M., McCarthy T. V., Vaughan P. M. (1997) Biochemical Society Transactions vol 25 p. 319–322.

Example 3

Three primers are made based on the *Thermomyces lanuginosa* lipase gene (EMBL accession no.: AF054513), where each primer contains two in-frame stopcodons (shown below in bold typeface) and a silent mutation (shown below in underlined italic typeface). In order to have a functional lipase gene, recombination has to take place between all three primers during the Recombinatorial Chain Reaction (RCR) method of the invention. After RCR the primers are subjected to a round of PCR and a cloning step.

The following reaction is mixed to a total of 25 microliter: 10 microliter of cell extract, 40 pmol of primer 251000j2, 40 pmol of primer 251000j3, 40 pmol of primer 251000j4 in buffer (20 mM Tris/HCl pH 7.5, 5 mM MgCl2, 0.1 mM Dithiothreitol, 0.1 mM EDTA).

251000j2 (SEQ ID NO:9): 5' atcgggaatcttaacttcgactagtaagaaatt*aat*gacatttgctcc 251000j3 (SEQ ID NO:10): 5' atcgggaatcttaacttcgactagaaataaatt*aat*gacatttgctcc 251000j4rev (SEQ ID NO:11): 5' ggagcaaatgtcatt*aatttatta*caagtcgaagttaagattcccgat The reaction-mix is placed in a PCR machine (e.g. Perkin Elmer® 2400) and the following Recombinatorial Chain Reaction (RCR) cycle was run 94° C. 5 min, 30 times (94° C., 30 sec., 45° C. 1 min, 72° C., 3 min). After the RCR reaction, the mix is purified by being spun on BioRad® Columns (Micro Bio-spin P-6™; Biorad®).

Two PCR reactions as listed below are run at the following protocol: 94° C., 5 min; 30 cycles of (94° C., 30 sec; 50° C., 1 min; 72° C., 2 min); 72° C., 5 min.
PCR1 (app. 420 bp):

Use pENI1298 as template, 20 pmol primer 19072000j1 and 1 microliter of the purified RCR extract in a total of 20 microliter, along with PWO™ DNA polymerase (Boehringer Mannheim™).
Primer 19072000J1 (SEQ ID NO:12):
5' ggggacaagtttgtacaaaaaagcaggcttctctgaacaataaaccccac
PCR2 (app.600 bp):

Use pENI1298 as template, 20 pmol primer 16062000j2 and 1 microliter of the purified RCR extract in a total of 20 microliter, along with PWO™ DNA polymerase (Boehringer Mannheim™).
Primer 16062000j2 (SEQ ID NO:13):
5' ggggaccactttgtacaagaaagctgggtcctagatctcgagctcggtcac The PCR fragments PCR1 and PCR2 are purified from a 1.5% agarose using a Qiagen™ gel extraction kit. A third PCR (PCR3) is run using 1 micro l of each purified PCR fragment, 20 pmol primer 16062000j2, 20 pmol primer 19072000j1 in a total of 20 microliter, along with PWO™ polymerase (Boehringer Mannheim™). The PCR fragment PCR3 is purified using BioRad™ Columns (Micro Bio-spin P-6™).

The BP cloning reaction is made by mixing the PCR3 fragment with BP reaction buffer, pDONR201 vector and BP clonase mix (as recommended by Lifetechnology®). Plasmid pENI1960 is cut with ScaI (in order to cleave in the ccdB gene), and mixed with the BP reaction and LR clonase mix (as recommended by Lifetechnology®) and transformed into *E. coli* DH10b (Life-Technology™ cat. no.18290–015).

The transformation is plated onto A+B minimal plates (Clark and Maaloe (1967) J. Mol Biol. Vol 23 p. 99–112) supplemented with 1% olive oil, ampicillin (100 microgram/ml) and 25 microgram/ml leucine. Only those *E. coli* transformants that have the plasmid and express a functional lipase will grow on these plates.

A DNA preparation is made from each transformant and sequenced to confirm the functionality of the lipase gene, as well as to identify the silent mutation originating from the primers, thus confirming the that the recombination event during the RCR has taken place as expected.

Example 4

Three primers are made based on the *Thermomyces lanuginosa* lipase gene. Each primer contains 2 in-frame stopcodons (shown below in bold typeface) and a silent mutation (shown below in underlined italic typeface). In order to have a functional lipase gene, recombination has to take place between all three primers during the Recombinatorial Chain Reaction (RCR) method of the invention. After RCR the primers are subjected to a round of PCR and a cloning step.

The following reaction is mixed in a total of 25 microliter: 10 microliter of cell extract, 40 pmol of primer 251000j2, 40 pmol of primer 251000j3, 40 pmol of primer 251000j4 in buffer (20 mM Tris/HCl pH 7.5, 5 mM MgCl2, o.1 mM Dithreitol, 0.1 mM EDTA).

The reaction-mix is placed in a PCR machine (e.g. Perkin Elmer® 2400) and the following Recombinatorial Chain Reaction (RCR) cycle was run 94° C. 5 min, 30 times (94° C., 30 sec., 45° C. 1 min, 72° C., 3 min). After the RCR reaction, the mix is purified by being spun on BioRad® Columns (Micro Bio-spin P-6™; Biorad®).

Two PCR reactions as listed below are run at the following protocol: 94° C., 5 min; 30 cycles of (94° C., 30 sec; 50° C., 1 min; 72° C., 2 min); 72° C., 5 min.

PCR 1 (app. 420 bp):

Use pENI1298 as template, 20 pmol primer 19671 and 1 microliter of the purified RCR extract in a total of 20 microliter, along with PWO™ DNA polymerase (Boehringer Mannheim™).

Primer 19671 (SEQ ID NO:14): 5' ctcccttctctgaa-caataaaccc

PCR 2 (app. 600 bp):

Use pENI1298 as template, 20 pmol primer 991213J5 and 1 microliter of the purified RCR extract in a total of 20 microliter, along with PWO™ DNA polymerase (Boehringer Mannheim™).

Primer 991213J5 (SEQ ID NO:15):
5' cctctagatctcgagctcggtcaccg-gtggcctccgcggccgctgcgccaggtgtcagtcaccctc The two PCR fragments PCR1 and PCR2 are purified from a 1.5% agarose using a Qiagen® gel extraction kit. A third PCR (PCR3) is run using 1 microliter of each purified PCR fragment, PCR1 and PCR2, 100 pmol primer 19671, 100 pmol primer 991213J5 in a total of 100 microliter, along with PWO™ polymerase (Boehringer Mannheim™). After the reaction, the PCR3 fragment is purified from the mix by being spun on BioRad™ Columns (Micro Bio-spin P-6™).

The PCR fragment PCR3 and pENI 1902 are both cut BamHI and SacII and the cut fragments are purified from a 1% agarose gel using a Qiagen™ gel extraction kit. The fragment and the pENI1902 vector are ligated and transformed into *E. coli* DH10b.

The transformation is plated onto A+B minimal plates (Clark and Maaloe (1967) J. Mol Biol. Vol 23 p. 99–112) supplemented with 1% olive oil, 100 microgram/ml ampicillin and 25 microgram/ml leucine. Only those *E. coli* transformants that have the plasmid and express a functional lipase will grow on these plates.

A DNA preparation is made from each transformant and sequenced to confirm the functionality of the lipase gene, as well as to identify the silent mutation originating from the primers, thus confirming the that the recombination event during the RCR has taken place as expected.

Example 5
Construction of the Expression Plasmid pMT2188

The *Aspergillus oryzae* expression plasmid pCaHj 483 (WO 98/00529) consists of an expression cassette based on the *Aspergillus niger* neutral amylase II promoter fused to the *Aspergillus nidulans* triose phosphate isomerase non translated leader sequence (Pna2/tpi) and the *A. niger* amyloglycosidase terminater (Tamg). Also present on the plasmid is the Aspergillus selective marker amdS from *A. nidulans* enabling growth on acetamide as sole nitrogen source. These elements are cloned into the *E. coli* vector pUC19 (New England Biolabs). The ampicillin resistance marker enabling selection in *E. coli* of this plasmid was replaced with the URA3 marker of *Saccharomyces cerevisiae* that can complement a pyrF mutation in *E. coli*, the replacement was done in the following way:

The pUC19 origin of replication was PCR amplified from pCaHj483 with the primers:

142779 (SEQ ID NO:16): 5' ttgaattgaaaatagattgatt-taaaacttc 142780 (SEQ ID NO:17): 5' ttgcatgcgtaatcatggtcatagc Primer 142780 introduces a BbuI site in the PCR fragment. The Expand PCR system (Roche Molecular Biochemicals, Basel, Switserland) was used for the amplification following the manufacturers instructions for this and the subsequent PCR amplifications.

The URA3 gene was amplified from the general *S. cerevisiae* cloning vector pYES2 (Invitrogen corporation, Carlsbad, Calif., USA) using the primers:

140288 (SEQ ID NO:18):
5' ttgaattcatgggtaataactgatat 142778 (SEQ ID NO:19):
5' aaatcaatctattttcaattcaattcatcatt Primer 140288 introduces an EcoRI site in the PCR fragment. The two PCR fragments were fused by mixing them and amplifying using the primers 142780 and 140288 in the splicing by overlap method (Horton et al (1989) Gene, 77, 61–68).

The resulting fragment was digested with EcoRI and BbuI and ligated to the largest fragment of pCaHj 483 digested with the same enzymes. The ligation mixture was used to transform the pyrF *E. coli* strain DB6507 (ATCC 35673) made competent by the method of Mandel and Higa (Mandel, M. and A. Higa (1970) J. Mol. Biol. 45, 154). Transformants were selected on solid M9 medium (Sambrook et. al (1989) Molecular cloning, a laboratory manual, 2. edition, Cold Spring Harbor Laboratory Press) supplemented with 1 g/l casaminoacids, 500 μg/l thiamine and 10 mg/l kanamycin.

A plasmid from a selected transformant was termed pCaHj 527. The Pna2/tpi promoter present on pCaHj527 was subjected to site directed mutagenises by a simple PCR approach. Nucleotide 134–144 was altered from GTAC-TAAAACC to CCGTTAAATTT using the mutagenic primer 141223.
141223 (SEQ ID NO:20):
5' ggatgctgttgactccggaaatttaacggtttggtcttgcatccc
Nucleotide 423–436 was altered from ATGCAATT-TAAACT to CGGCAATTTAACGG using the mutagenic primer 141222:
141222 (SEQ ID NO:21):
5'ggtattgtcctgcagacggcaatttaacggcttctgcgaatcgc
The resulting plasmid was termed pMT2188.

Example 6

Three primers were made based on the *Thermomyces lanuginosa* lipase gene (EMBL accession no.: AF054513), where each primer contained two in-frame stop codons (shown below in bold typeface) and a silent mutation (shown below in underlined italic typeface). The following reactions were mixed to a total of 25 microliter: Either 0.1 microliter, 1 microliter or 10 microliter of cell extract (re-suspended in gel-filtration buffer after $(NH_4)_2SO_4$ precipitation), 40 pmol of primer 251000j2, 40 pmol of primer 251000j3, 40 pmol of primer 251000j4 in buffer (20 mM Tris/HCl pH 7.5, 5 mM $MgCl_2$, 0.1 mM Dithiothreitol, 0.1 mM EDTA).

Primer 251000j2 (SEQ ID NO:9); primer 251000j3 (SEQ ID NO:10); and primer 251000j4 (SEQ ID NO:22):
5'atcgggaatcttaacttcgacttgtaataaattaatgacatttgctcc The reaction-mixes were placed in a PCR machine (e.g. Perkin Elmer® 2400) and the following Recombinatorial Chain Reaction (RCR) cycle was run 94° C. 1 min, 30 times (94° C., 30 sec., 45° C. 1 min, 72° C., 3 min).

Two PCR reactions as listed below were run at the following protocol: 94° C., 5 min; 30 cycles of (94° C., 30 sec; 50° C., 1 min; 72° C., 2 min); 72° C., 5 min.

PCR1 (app. 420 bp):

Using pENI1298 as template, 20 pmol primer 19671 and primer 251000J5 in a total of 20 microliter, along with PWO™ DNA polymerase (Boehringer Mannheim™) including buffer and dNTP.

Primer 251000J5 (SEQ ID NO:23): 5' gtcgaagttaagattcccgat

Primer 19671 (SEQ ID NO:24): 5' ctcccttctctgaacaataaaccc

PCR2 (app.600 bp):

Using pENI1298 as template, 20 pmol primer 115120 and 1 microliter of the RCR extract (either originating from 0.1 microliter, 1 microliter or 10 microliter of cell extract) in a total of 20 microliter, along with PWO™ DNA polymerase (Boehringer Mannheim™) including buffer and dNTP.
Primer 115120 (SEQ ID NO:25): 5' gctttgtgcagggtaaatc The PCR fragments PCR1 and PCR2 were purified from a 1.5% agarose using a Qiagen™ gel extraction kit. A third PCR (PCR3) was run using 1 microliter of each purified PCR fragment, 20 pmol primer 19671, 20 pmol primer 991213J5 in a total of 20 microliter, along with PWO™ polymerase (Boehringer Mannheim™) including buffer and dNTP. The PCR fragment PCR3 was purified using Bio-Rad™ Columns (Micro Bio-spin P-6™).
Primer 991213J5 (SEQ ID NO:26):
5' cctctagatctcgagctcggtcaccg-gtggcctccgcggccgctgcgccaggtgtcagtcaccctc The PCR fragment PCR3 and a pENI 1902-derivative were both cut BamHI and SacII and the cut fragments were purified from a 1% agarose gel using a Qiagen™ gel extraction kit. The fragment and the pENI1902-derived vector were ligated and transformed into *E. coli* DH10b.

A DNA preparation was made from 6 transformant and sequenced. Recombination had taken place in at least one case.

Example 7

Three primers were made based on the *Thermomyces lanuginosa* lipase gene (EMBL accession no.: AF054513), where each primer contained two in-frame stop codons (shown below in bold typeface) and a silent mutation (shown below in underlined italic typeface).

The following reactions are mixed to a total of 25 microliter: Either 0.1 microliter, 1 microliter or 10 microliter of cell extract (re-suspended in gel-filtration buffer after (NH$_4$)$_2$SO$_4$ precipitation), 40 pmol of primer 251000j2, 40 pmol of primer 251000j3, 40 pmol of primer 070801J1 in buffer (20 mM Tris/HCl pH 7.5, 5 mM MgCl$_2$, 0.1 mM EDTA, 1 mM ATP, 10% glycerol).
Primer 251000j2 (SEQ ID NO:9); Primer 251000j3 (SEQ ID NO:10); and Primer 070801J1 (SEQ ID NO:27): 5' ggag-caaatgtcatt*aa*tttattacaagtcgaagttaagattcccgat The reaction-mix is placed in a PCR machine (e.g. Perkin Elmer® 2400) and the following Recombinatorial Chain Reaction (RCR) cycle was run 94° C. 5 min, 30 times (94° C., 30 sec., 45° C. 1 min, 72° C., 3 min).

Two PCR reactions as listed below are run at the following protocol: 94° C., 1 min; 30 cycles of (94° C., 30 sec; 50° C., 1 min; 72° C., 2 min); 72° C., 5 min.

PCR 1 (app. 420 bp):

Use pENI1298 as template, 20 pmol primer 19671 (SEQ ID NO:14) and 1 microliter of the purified RCR extract (either originating from 0.1 microliter, 1 microliter or 10 microliter of cell extract) in a total of 20 microliter, along with PWO™ DNA polymerase (Boehringer Mannheim™).

PCR 2 (app.600 bp):

Use pENI1298 as template, 20 pmol primer 991213J5 (SEQ ID NO:15) and 1 microliter of the purified RCR extract (either originating from 0.1 microliter, 1 microliter or 10 microliter of cell extract) in a total of 20 microliter, along with PWO™ DNA polymerase (Boehringer Mannheim™).

The two PCR fragments from PCR1 and PCR2 are purified from a 1.5% agarose using a Qiagen® gel extraction kit. A third PCR (PCR3) is run using 1 microliter of each purified PCR fragment, PCR1 and PCR2, 100 pmol primer 19671, 100 pmol primer 991213J5 in a total of 100 microliter, along with PWO™ polymerase (Boehringer Mannheim™). After the reaction, the PCR3 fragment is purified from the mix by being spun on BioRad™ Columns (Micro Biospin P-6™).

The PCR fragment PCR3 and pENI1861 are both cut BamHI and SacII and the cut fragments are purified from a 1% agarose gel using a Qiagen™ gel extraction kit. The fragment and the pENI1861 vector are ligated and transformed into *E. coli* DH10b.

The transformation are plated onto both LB-plates containing 100 microgram/ml ampicillin and onto A+B minimal plates (Clark and Maaloe (1967) J. Mol Biol. Vol 23 p. 99–112) supplemented with 1% olive oil, 100 microgram/ml ampicillin and 25 microgram/ml leucine. Only those *E. coli* transformants that have the plasmid and express a functional lipase will grow on A+B minimal plates (Clark and Maaloe (1967) J. Mol Biol. Vol 23 p. 99–112) supplemented with 1% olive oil, 100 microgram/ml ampicillin and 25 microgram/ml leucin.

A DNA preparation is made from each transformant, and sequenced to confirm the functionality of the lipase gene, as well as to identify the silent mutation originating from the primers, thus confirming the that the recombination event during the RCR has taken place as expected.

A DNA preparation is made from each transformant growing on the LB-plates containing 100 microgram/ml ampicillin, and sequenced to confirm that mutations have been recombined, as well as to identify the silent mutation originating from the primers, thus confirming the that the recombination event during the RCR has taken place as expected.

What is claim is:

1. A method for forming a plurality of recombined homologous double-stranded polynucleotides from at least two homologous double-stranded template polynucleotides, said method comprising the steps of:
   a) providing a solution comprising at least two non-methylated homologous double-stranded template polynucleotides and one or more thermostable mismatch repair protein(s);
   b) denaturing the template polynucleotides into single-stranded polynucleoides by increasing the temperature of the solution;
   c) annealing the different single-stranded polynucleotides by lowering the temperature of the solution, wherein heteroduplexes are formed;
   d) allowing the thermostable mismatch repair protein(s) to repair nucleotide mismatches in the heteroduplexes, wherein recombined new duplexes are formed; and
   e) repeating steps b) through d) at least once; wherein the new duplexes of step d) serve as new template polynucleotides in step b) in each repetition.

2. The method of claim 1, wherein the at least two homologous double-stranded template polynucleotides are obtained by PCR amplification.

3. The method of claim 1 or 2, wherein the at least two homologous double-stranded template polynucleotides encode homologous polypeptides.

4. The method of claim 1, wherein the at least two homologous double-stranded template polynucleotides encode homologous enzymes.

5. The method of claim 1, wherein the solution comprises a population of cells or a lysate of a population of cells.

6. The method of claim 5, wherein the population of cells or the lysate of a population of cells comprises the at least two homologous double-stranded template polynucleotides.

7. The method of claim 5, wherein the population of cells or the lysate of a population of cells comprises the mismatch repair protein(s).

8. The method of claim 5, wherein the population of cells, or the population of cells giving rise to the lysate, do not methylate newly synthesized polynucleotides.

9. The method of claim 1, wherein the thermostable mismatch repair protein(s) comprises a MutS homologue.

10. The method of claim 1, wherein the thermostable mismatch repair protein(s) comprises a MutL homologue, a MSH2 homologue, a MSH6 homologue, a MutM homologue, a MutY homologue, a MutT homologue, a MutH homologue, a HexA homologue, a HexB homologue, or a GTBP/p160 homolog.

11. The method of claim 1, wherein the denaturing is achieved by increasing the temperature of the solution to at least 90° C.

12. The method of claim 11, wherein the annealing is achieved by lowering the temperature of the solution to between 55° C. and 75° C.

13. The method of claim 1, wherein steps b) through d) are repeated for between 1 and 10 cycles; wherein the new duplexes of step d) serve as new template polynucleotides in step b) in each repetition.

14. The method of claim 1, wherein steps b) through d) are repeated for at least 10 cycles; wherein the new duplexes of step d) serve as new template polynucleotides In step b) in each repetition.

15. The method of claim 1, wherein additional steps are performed, said additional steps comprising:

f) generating a gene library by cloning the plurality of recombined polynucleotides;

g) expressing and screening the gene library for an activity or property of interest; and h) isolating or identifying the recombined polynucleotide which gives rise to the activity or property of interest.

16. The method of claim 4, wherein the at least two homologous double-stranded template polynucleotides encode amylases, proteases, cellulsases, lipases, xylanases or phospholipases.

17. The method of claim 1, wherein the thermostable mismatch repair protein(s) comprises MutS YT1 of *Thermus aquaticus*.

* * * * *

SEQUENCE LISTING

<160> NUMBER OF SEQ ID NOS: 27

<210> SEQ ID NO 1
<211> LENGTH: 30
<212> TYPE: DNA
<213> ORGANISM: Artificial sequence
<220> FEATURE:
<223> OTHER INFORMATION: Primer
<221> NAME/KEY: misc_feature
<222> LOCATION: (1)..(1)
<223> OTHER INFORMATION: 5' Phosphorylation

<400> SEQUENCE: 1
gaatgacttg gttgacgcgt caccagtcac                              30

<210> SEQ ID NO 2
<211> LENGTH: 25
<212> TYPE: DNA
<213> ORGANISM: Artificial sequence
<220> FEATURE:
<223> OTHER INFORMATION: Primer
<221> NAME/KEY: misc_feature
<222> LOCATION: (1)..(1)
<223> OTHER INFORMATION: 5' Phosphorylation

<400> SEQUENCE: 2
cttattagta ggttggtact tcgag                                   25

<210> SEQ ID NO 3
<211> LENGTH: 37
<212> TYPE: DNA
<213> ORGANISM: Artificial sequence
<220> FEATURE:
<223> OTHER INFORMATION: Primer
<221> NAME/KEY: misc_feature
<222> LOCATION: (1)..(1)
<223> OTHER INFORMATION: 5' Phosphorylation

<400> SEQUENCE: 3
gtccccagag tagtgtcact atgtcgaggc agttaag                      37

<210> SEQ ID NO 4
<211> LENGTH: 64
<212> TYPE: DNA
<213> ORGANISM: Artificial sequence
<220> FEATURE:
<223> OTHER INFORMATION: Primer
<221> NAME/KEY: misc_feature
<222> LOCATION: (1)..(1)
<223> OTHER INFORMATION: 5' Phosphorylation

<400> SEQUENCE: 4
gtatgtccct tgacaatgcg atgtatcaca tgatataatt actagcaagg gaagccgtgc    60
ttgg                                                                64

<210> SEQ ID NO 5
<211> LENGTH: 59
<212> TYPE: DNA
<213> ORGANISM: Artificial sequence
<220> FEATURE:
<223> OTHER INFORMATION: Primer

<400> SEQUENCE: 5
cctctagatc tcgagctcgg tcaccggtgg cctccgcggc cgctggatcc ccagttgtg     59

<210> SEQ ID NO 6
<211> LENGTH: 33
<212> TYPE: DNA
<213> ORGANISM: Artificial sequence
<220> FEATURE:
<223> OTHER INFORMATION: Primer

<400> SEQUENCE: 6
gcaagcgcgc gcaatacatg gtgttttgat cat                            33

<210> SEQ ID NO 7
<211> LENGTH: 26
<212> TYPE: DNA
<213> ORGANISM: Artificial sequence
<220> FEATURE:
<223> OTHER INFORMATION: Primer

<400> SEQUENCE: 7
tctgtgaggc ctatggatct cagaac                                    26

<210> SEQ ID NO 8
<211> LENGTH: 27
<212> TYPE: DNA
<213> ORGANISM: Artificial sequence
<220> FEATURE:
<223> OTHER INFORMATION: Primer

<400> SEQUENCE: 8
gatgctgcat gcacaactgc acctcag                                   27

<210> SEQ ID NO 9
<211> LENGTH: 48
<212> TYPE: DNA
<213> ORGANISM: Artificial sequence
<220> FEATURE:
<223> OTHER INFORMATION: Primer
<221> NAME/KEY: misc_signal
<222> LOCATION: (22)..(27)
<223> OTHER INFORMATION: Two stop-codons
<221> NAME/KEY: misc_signal
<222> LOCATION: (33)..(33)
<223> OTHER INFORMATION: Silent mutation

<400> SEQUENCE: 9
atcgggaatc ttaacttcga ctagtaagaa attaatgaca tttgctcc            48

<210> SEQ ID NO 10
<211> LENGTH: 48
<212> TYPE: DNA
<213> ORGANISM: Artificial sequence
<220> FEATURE:
<223> OTHER INFORMATION: Primer
<221> NAME/KEY: misc_signal
<222> LOCATION: (22)..(24)
<223> OTHER INFORMATION: Stop-codon
<221> NAME/KEY: misc_signal
<222> LOCATION: (28)..(30)
<223> OTHER INFORMATION: Stop-codon
<221> NAME/KEY: misc_signal
<222> LOCATION: (33)..(33)
<223> OTHER INFORMATION: Silent mutation

<400> SEQUENCE: 10
atcgggaatc ttaacttcga ctagaaataa attaatgaca tttgctcc            48

<210> SEQ ID NO 11
<211> LENGTH: 48
<212> TYPE: DNA
<213> ORGANISM: Artificial sequence

```
<220> FEATURE:
<223> OTHER INFORMATION: Primer
<221> NAME/KEY: misc_signal
<222> LOCATION: (16)..(16)
<223> OTHER INFORMATION: Silent mutation
<221> NAME/KEY: misc_signal
<222> LOCATION: (19)..(24)
<223> OTHER INFORMATION: Two Stop-codons

<400> SEQUENCE: 11
ggagcaaatg tcattaattt attacaagtc gaagttaaga ttcccgat          48

<210> SEQ ID NO 12
<211> LENGTH: 50
<212> TYPE: DNA
<213> ORGANISM: Artificial sequence
<220> FEATURE:
<223> OTHER INFORMATION: Primer

<400> SEQUENCE: 12
ggggacaagt ttgtacaaaa aagcaggctt ctctgaacaa taaaccccac         50

<210> SEQ ID NO 13
<211> LENGTH: 51
<212> TYPE: DNA
<213> ORGANISM: Artificial sequence
<220> FEATURE:
<223> OTHER INFORMATION: Primer

<400> SEQUENCE: 13
ggggaccact ttgtacaaga aagctgggtc ctagatctcg agctcggtca c       51

<210> SEQ ID NO 14
<211> LENGTH: 24
<212> TYPE: DNA
<213> ORGANISM: Artificial sequence
<220> FEATURE:
<223> OTHER INFORMATION: Primer

<400> SEQUENCE: 14
ctcccttctc tgaacaataa accc                                    24

<210> SEQ ID NO 15
<211> LENGTH: 66
<212> TYPE: DNA
<213> ORGANISM: Artificial sequence
<220> FEATURE:
<223> OTHER INFORMATION: Primer

<400> SEQUENCE: 15
cctctagatc tcgagctcgg tcaccggtgg cctccgcggc cgctgcgcca ggtgtcagtc   60
accctc                                                        66

<210> SEQ ID NO 16
<211> LENGTH: 31
<212> TYPE: DNA
<213> ORGANISM: Artificial sequence
<220> FEATURE:
<223> OTHER INFORMATION: Primer

<400> SEQUENCE: 16
ttgaattgaa aatagattga tttaaaactt c                            31

<210> SEQ ID NO 17
<211> LENGTH: 25
<212> TYPE: DNA
```

```
<213> ORGANISM: Artificial sequence
<220> FEATURE:
<223> OTHER INFORMATION: Primer

<400> SEQUENCE: 17
ttgcatgcgt aatcatggtc atagc                                    25

<210> SEQ ID NO 18
<211> LENGTH: 26
<212> TYPE: DNA
<213> ORGANISM: Artificial sequence
<220> FEATURE:
<223> OTHER INFORMATION: Primer

<400> SEQUENCE: 18
ttgaattcat gggtaataac tgatat                                   26

<210> SEQ ID NO 19
<211> LENGTH: 32
<212> TYPE: DNA
<213> ORGANISM: Artificial sequence
<220> FEATURE:
<223> OTHER INFORMATION: Primer

<400> SEQUENCE: 19
aaatcaatct attttcaatt caattcatca tt                            32

<210> SEQ ID NO 20
<211> LENGTH: 45
<212> TYPE: DNA
<213> ORGANISM: Artificial sequence
<220> FEATURE:
<223> OTHER INFORMATION: Primer

<400> SEQUENCE: 20
ggatgctgtt gactccggaa atttaacggt ttggtcttgc atccc              45

<210> SEQ ID NO 21
<211> LENGTH: 44
<212> TYPE: DNA
<213> ORGANISM: artificial sequence
<220> FEATURE:
<223> OTHER INFORMATION: Primer

<400> SEQUENCE: 21
ggtattgtcc tgcagacggc aatttaacgg cttctgcgaa tcgc               44

<210> SEQ ID NO 22
<211> LENGTH: 48
<212> TYPE: DNA
<213> ORGANISM: Artificial sequence
<220> FEATURE:
<223> OTHER INFORMATION: Primer

<400> SEQUENCE: 22
atcgggaatc ttaacttcga cttgtaataa attaatgaca tttgctcc           48

<210> SEQ ID NO 23
<211> LENGTH: 21
<212> TYPE: DNA
<213> ORGANISM: Artificial sequence
<220> FEATURE:
<223> OTHER INFORMATION: Primer

<400> SEQUENCE: 23
gtcgaagtta agattcccga t                                        21
```

```
<210> SEQ ID NO 24
<211> LENGTH: 24
<212> TYPE: DNA
<213> ORGANISM: Artificial sequence
<220> FEATURE:
<223> OTHER INFORMATION: Primer

<400> SEQUENCE: 24
ctcccttctc tgaacaataa accc                                          24

<210> SEQ ID NO 25
<211> LENGTH: 19
<212> TYPE: DNA
<213> ORGANISM: Artificial sequence
<220> FEATURE:
<223> OTHER INFORMATION: Primer

<400> SEQUENCE: 25
gctttgtgca gggtaaatc                                                19

<210> SEQ ID NO 26
<211> LENGTH: 66
<212> TYPE: DNA
<213> ORGANISM: Artificial sequence
<220> FEATURE:
<223> OTHER INFORMATION: Primer

<400> SEQUENCE: 26
cctctagatc tcgagctcgg tcaccggtgg cctccgcggc cgctgcgcca ggtgtcagtc   60
accctc                                                              66

<210> SEQ ID NO 27
<211> LENGTH: 48
<212> TYPE: DNA
<213> ORGANISM: Artificial sequence
<220> FEATURE:
<223> OTHER INFORMATION: Primer

<400> SEQUENCE: 27
ggagcaaatg tcattaattt attacaagtc gaagttaaga ttccccgat               48
```